US00PP13896P39

(12) United States Plant Patent
Bergman

(10) Patent No.: US PP13,896 P3
(45) Date of Patent: Jun. 17, 2003

(54) CHRYSANTHEMUM PLANT NAMED 'YOPRESIDIO'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 78 days.

(21) Appl. No.: 09/955,839

(22) Filed: Sep. 20, 2001

(65) Prior Publication Data

US 2003/0056265 P1 Mar. 20, 2003

(51) Int. Cl.[7] ..... A01H 5/00

(52) U.S. Cl. ..... Plt./291

(58) Field of Search ..... Plt./287, 291

*Primary Examiner*—Howard J. Locker
(74) *Attorney, Agent, or Firm*—C. A. Whealy

(57) ABSTRACT

A distinct cultivar of Chrysanthemum plant named 'Yopresidio', characterized by its uniform plant habit; strong and freely branching growth habit; dark green foliage; uniform and freely flowering habit; early flowering, eight-week response time; decorative-type inflorescences that are about 11.2 cm in diameter; pink-colored ray florets; good postproduction longevity with plants maintaining good substance and color for about three to four weeks in an interior environment; and tolerance to high production temperatures and low light conditions.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yopresidio'.

The new Chrysanthemum is a product of a planned breeding program conducted by the Inventor in Fort Myers, Fla. and Salinas, Calif. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in February, 1997, in Salinas, Calif., of a proprietary Chrysanthemum seedling selection identified as code number YB-6835, not patented, as the female, or seed, parent with a proprietary Chrysanthemum seedling selection identified as code number YB-4274, not patented, as the male, or pollen, parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and floret colors, fast response time, and excellent postproduction longevity.

Asexual reproduction of the new Chrysanthemum by vegetative tip cuttings was first conducted in Fort Myers, Fla. in March, 1998. Asexual reproduction by cuttings has shown that the unique features of this new Chrysanthemum are stable and reproduced true to type in successive generations.

SUMMARY OF THE INVENTION

The cultivar Yopresidio has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yopresidio'. These characteristics in combination distinguish 'Yopresidio' as a new and distinct Chrysanthemum:

1. Uniform plant habit.
2. Strong and freely branching growth habit.
3. Dark green foliage.
4. Uniform and freely flowering habit.
5. Can be grown as a disbud or spray-type.
6. Early flowering, eight-week response time.
7. Decorative-type inflorescences that are about 11.2 cm in diameter.
8. Pink-colored ray florets.
9. Good postproduction longevity with plants maintaining good substance and color for about three to four weeks in an interior environment.
10. Tolerant to high production temperatures and low light conditions.

Compared to plants of the female parent selection, plants of the new Chrysanthemum are more outwardly spreading and flower more uniformly. In addition, plants of the new Chrysanthemum have pink-colored ray florets whereas plants of the female parent have white-colored ray florets.

Compared to plants of the male parent selection, plants of the new Chrysanthemum are more vigorous and have a more fully double inflorescence form.

Plants of the new Chrysanthemum can be compared to plants of the cultivar Charm, disclosed in U.S. Plant Pat. No. 5,502. In side-by-side comparisons conducted by the Inventor in Salina, Calif. plants of the new Chrysanthemum differed from plants of the cultivar Charm in the following characteristics:

1. Plants of the new Chrysanthemum were more vigorous and denser than plants of the cultivar Charm.

2. Ray floret color of plants of the new Chrysanthemum was lighter than ray floret color of plants of the cultivar Charm.

3. Plants of the new Chrysanthemum were more high temperature tolerant than plants of the cultivar Charm.

Plants of the new Chrysanthemum can also be compared to plants of the cultivar Yolansing, disclosed in U.S. Plant Pat. No. 11,209. In side-by-side comparisons conducted by the Inventor in Salinas, Calif. plants of the new Chrysanthemum differed from plants of the cultivar Yolansing in the following characteristics:

1. Plants of the new Chrysanthemum had a stronger growth habit than plants of the cultivar Yolansing.

2. Inflorescences of plants of the new Chrysanthemum had a more fully double form than inflorescences of plants of the cultivar Yolansing.

3. Ray floret color of plants of the new Chrysanthemum was lighter than ray floret color of plants of the cultivar Yolansing.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Yopresidio' grown as a disbud-type.

The photograph on the second sheet comprises a close-up view of typical inflorescences of 'Yopresidio' grown as a disbud-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of pinching, the photoinductive short day/long night treatments were started. Plants used for this description were grown as disbud-types. Measurements and numerical values represent averages of typical flowering plants.

Botanical classification: *Chrysanthemum×morifolium* cultivar Yopresidio.

Commercial classification: Decorative-type potted Chrysanthemum.

Parentage:

*Female, or seed, parent.*—Proprietary *Chrysanthemum×morifolium* seedling selection identified as code number YB-6835, not patented.

*Male, or pollen, parent.*—Proprietary *Chrysanthemum×morifolium* seedling selection identified as code number YB-4274, not patented.

Propagtion:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous decorative-type potted Chrysanthemum that can be grown as a disbud or as a spray-type. Stems mostly upright and somewhat outwardly spreading; uniform crown. Very freely branching, about four or five lateral branches develop after removal of terminal apex (pinching); dense and full plants.

*Plant height.*—About 38 cm.

*Plant width.*—About 49 cm.

*Lateral branches* (*peduncles*).—Length: About 34 cm. Diameter: About 6 mm. Internode length: About 2.3 cm. Strength: Strong. Texture: Pubescent. Color: 146A. Foliage description Arrangement: Alternate. Quantity of leaves per lateral stem: About 13. Length: About 9.8 cm. Width: About 7.5 cm. Apex: Cuspidate to mucronate. Base: Attenuate to truncate. Margin: Palmately lobed, sinuses between lateral lobes parallel, divergent or convergent. Texture: Upper and lower surfaces with very fine pubescence; veins prominent on lower surface. Color: Young foliage, upper surface: Darker than 1 47A. Young foliage, lower surface: Darker than 147B. Mature foliage, upper surface: Darker than 147A. Mature foliage, lower surface: Closest to 147B. Venation, upper & lower surfaces: Close to 146C. Petiole length: About 2.2 cm. Petiole diameter: About 3 mm. Petiole color: Close to 146C.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant. Can be grown as a disbud or spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 47 to 53 days later when grown as a disbud-type and about 54 to 59 days later when grown as a spray-type.

*Postproduction longevity.*—Inflorescences maintain good color and substance for at about three to four weeks in an interior environment.

*Quantity of inflorescences.*—Grown as a disbud-type, only one inflorescence, the terminal, develops per lateral branch.

*Inflorescence bud.*—Height: About 8 mm. Diameter: About 1.1 cm. Color: Close to 137A.

*Inflorescence size.*—Diameter: About 11.2 cm. Depth (height): About 3.7 cm. Diameter of disc: About 5 mm; inconspicuous. Receptacle diameter: About 1 cm.

*Ray florets.*—Shape: Elongated-oblong. Orientation: Initially upright, then perpendicular to peduncle. Aspect: Initially in curved to slightly reflexed. Length: About 5.3 cm. Width: About 1.3 cm. Apex: Acute, rounded or emarginate. Base: Attenuate; short corolla tube. Corolla tube length: About 5 mm. Margin: Entire. Texture: Smooth, glabrous, satiny. Number of ray florets per inflorescence: About 195 arranged in numerous rows. Color: When opening and fully expanded, upper surface: Closest to 65B to 65D. When opening and fully expanded, lower surface: Closest to 65D to 155D.

*Disc florets.*—Arrangement: Massed at center of receptacle. Shape: Tubular, elongated. Apex: Five-pointed. Length: About 7 mm. Width: Apex: About 2 mm. Base: About 1 mm. Number of disc florets per inflorescence: About 10. Color: Immature: 154A. Mature: Apex: 9A. Mid-section: Closest to 145C. Base: Closest to 155D.

*Reproductive organs.*—Androecium: Present on disc florets only. Anther color: 9A. Pollen: None observed. Gynoecium: Present on both ray and disc florets.

*Seed.*—Seed production has not been observed.

Disease resistance: Resistance to pathogens common to Chrysanthemums has not been observed on plants grown under commercial greenhouse conditions.

Hight temperature tolerance: Plants of the new Chrysanthemum have been observed to be tolerant to high temperature conditions when grown during the summer under greenhouse conditions in southwest Florida.

Low light tolerance: Plants of the new Chrysanthemum have been observed to be tolerant to low light conditions when grown during the winter under greenhouse conditions in the northern United States.

It is claimed:

1. A new and distinct cultivar of Chrysanthemum plant named 'Yopresidio', as illustrated and described.

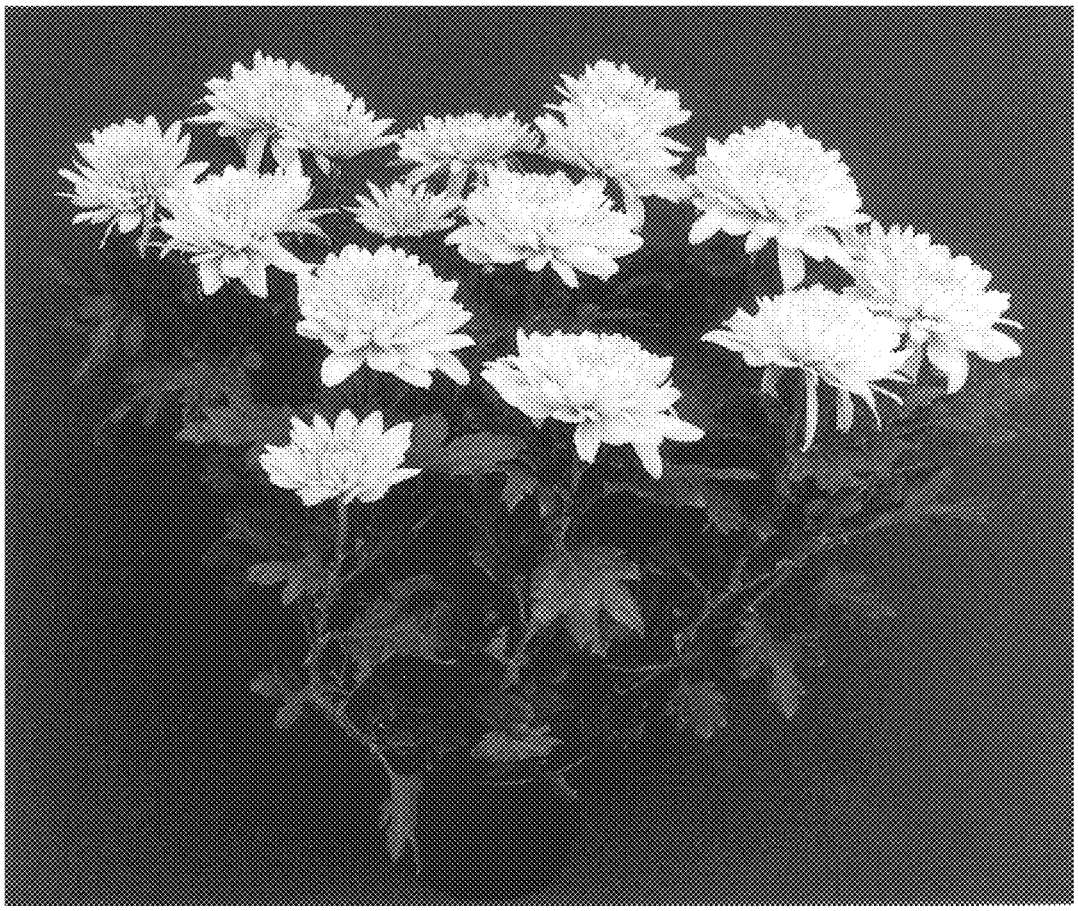

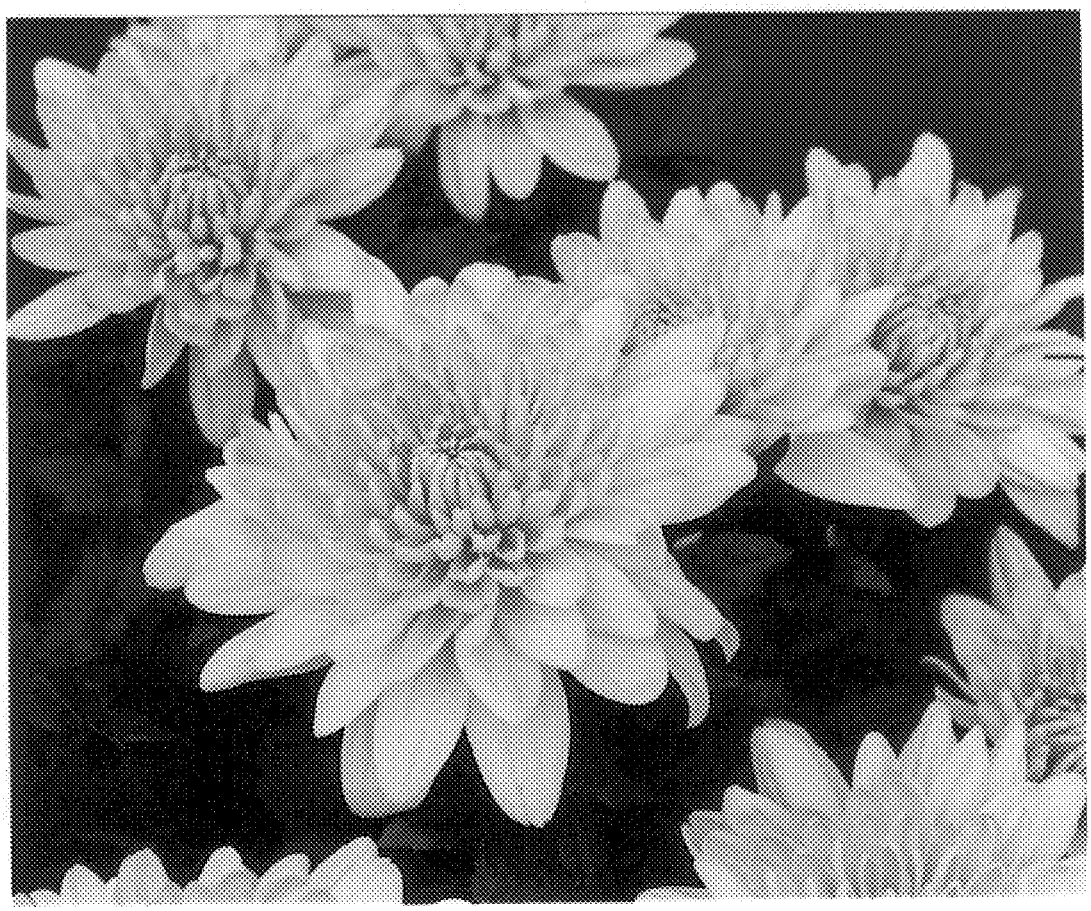

* * * * *